US010766843B2

United States Patent
Kim et al.

(10) Patent No.: US 10,766,843 B2
(45) Date of Patent: Sep. 8, 2020

(54) METHOD FOR PURIFYING PHENOL

(71) Applicant: LG CHEM, LTD., Seoul (KR)

(72) Inventors: Sung-Kyun Kim, Daejeon (KR);
Sung-Kyu Lee, Daejeon (KR);
Yeon-Uk Choo, Daejeon (KR);
Joon-Ho Shin, Daejeon (KR); Ha-Na Lee, Daejeon (KR); Tae-Woo Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 309 days.

(21) Appl. No.: 15/742,980

(22) PCT Filed: Oct. 11, 2016

(86) PCT No.: PCT/KR2016/011375
§ 371 (c)(1),
(2) Date: Jan. 9, 2018

(87) PCT Pub. No.: WO2017/069448
PCT Pub. Date: Apr. 27, 2017

(65) Prior Publication Data
US 2020/0079716 A1 Mar. 12, 2020

(30) Foreign Application Priority Data

Oct. 22, 2015 (KR) .................. 10-2015-0147417

(51) Int. Cl.
*C07C 37/78* (2006.01)
*B01D 3/14* (2006.01)
(Continued)

(52) U.S. Cl.
CPC .............. *C07C 37/78* (2013.01); *B01D 3/007* (2013.01); *B01D 3/06* (2013.01); *B01D 3/143* (2013.01); *B01D 3/36* (2013.01); *B01D 5/0063* (2013.01)

(58) Field of Classification Search
CPC ......... C07C 37/74; C07C 37/78; C07C 39/04; C07C 45/82; C07C 49/08; B01D 3/007;
(Continued)

(56) References Cited

U.S. PATENT DOCUMENTS 3,405,038 A * 10/1968 Kohmoto .............. C07C 37/685
203/69
4,298,765 A * 11/1981 Cochran ................ B01D 3/322
203/36
(Continued)

FOREIGN PATENT DOCUMENTS

DE          134 427 A3     2/1979
JP           68-65234 A     4/1983
(Continued)

OTHER PUBLICATIONS

Mao, W.,"Study on the Excessive Amounts of Heavy Components in Crude Phenol Tower Bottom on Distillation Process of Cumene Method for Phenol-Acetone Production", China Full-text Database of Excellent Master Degree Thesis (Engineering Science and Technology I), Dalian University of Technology, Sep. 15, 2013, pp. 15-18.

*Primary Examiner* — Jonathan Miller
(74) *Attorney, Agent, or Firm* — Dentons US LLP (57) ABSTRACT

Disclosed is a method for purifying phenol, by which the loss of a heat source is minimized, the amount used of steam is decreased, and efficiency of energy consumed in a process may be maximized. The method for purifying phenol includes a step of passing impurities including phenol, acetone and hydrocarbon, which are prepared using cumene as a raw material, via a plurality of distillation columns one by one, and performing azeotropic distillation, wherein the ratio of phenol and water at the uppermost end of the distillation column where the azeotropic distillation is per- (Continued)

formed, is from 60:40 to 65:35, for the optimized separation of the hydrocarbon.

9 Claims, 5 Drawing Sheets

(51) Int. Cl.
  *B01D 3/00* (2006.01)
  *B01D 3/06* (2006.01)
  *B01D 3/36* (2006.01)
  *B01D 5/00* (2006.01)

(58) Field of Classification Search
  CPC . B01D 3/06; B01D 3/143; B01D 3/36; B01D 5/0063
  See application file for complete search history.

(56) References Cited

U.S. PATENT DOCUMENTS

| | | | |
|---|---|---|---|
| 4,333,801 A | 6/1982 | Pujado | |
| 4,351,967 A * | 9/1982 | Nishimura | C07C 37/08 203/64 |
| 4,504,364 A | 3/1985 | Chen et al. | |
| 4,532,012 A | 7/1985 | Khonsari et al. | |
| 4,851,086 A * | 7/1989 | Khonsari | B01D 3/38 203/38 |
| 4,857,151 A * | 8/1989 | Suciu | B01D 3/34 203/82 |
| 6,225,513 B1 | 5/2001 | Zakoshansky et al. | |
| 6,486,365 B1 | 11/2002 | Fulmer et al. | |
| 8,865,957 B2 * | 10/2014 | Keenan | C07C 1/20 585/435 |
| 2002/0066661 A1 | 6/2002 | Schwarz et al. | |
| 2003/0221948 A1 | 12/2003 | Bortolo et al. | |
| 2005/0137429 A1 | 6/2005 | Tatake et al. | |
| 2014/0330044 A1 * | 11/2014 | Kuechler | C07C 37/07 568/376 |

FOREIGN PATENT DOCUMENTS

| | | |
|---|---|---|
| JP | 69-20239 A | 2/1984 |
| JP | 2000-86559 A | 3/2000 |
| JP | 2001-506251 A | 5/2001 |
| JP | 2005-521739 A | 7/2005 |
| JP | 2007-514781 A | 6/2007 |
| JP | 4540943 B2 | 9/2010 |
| KR | 10-1998-0023844 A | 7/1998 |
| KR | 10-2003-0060976 A | 7/2003 |
| KR | 10-0377297 B1 | 9/2003 |
| KR | 10-0516765 B1 | 9/2005 |
| KR | 10-2006-0130073 A | 12/2006 |
| KR | 10-1304294 B1 | 9/2013 |

* cited by examiner

METHOD FOR PURIFYING PHENOL

TECHNICAL FIELD

This application is the national stage of International Application No. PCT/KR2016/011375 filed on Oct. 11, 2016, and claims the benefit of Korean Application No. 10-2015-0147417, filed on Oct. 22, 2015, all of which are hereby incorporated by reference in their entirety for all purposes as if fully set forth herein.

The present invention relates to a method for purifying phenol which is prepared using cumene as a raw material, and more particularly, to a method for purifying phenol by which the loss of a heat source is minimized, the amount used of steam is decreased, and efficiency of energy consumed in a process may be maximized.

BACKGROUND ART

In order to prepare phenol prior to purifying phenol, a method for separately preparing phenol and acetone using an indirect oxidation reaction, etc. and using cumene, which is commonly synthesized from a phenol resin, nylon-6, an epoxy resin, a polycarbonate resin and a solvent, as a raw material, as shown in Reaction 1 below is used.

[Reaction 1]

The reaction product thus prepared includes impurities, and in order to remove thereof, a separation process with a plurality of steps which consume a large amount of energy is required. For example, a hydrocarbon removal column (HRC) for separating hydrocarbon materials having a similar boiling point as phenol via azeotropic distillation uses high pressure (HP) at the bottom thereof, and a low pressure (LP) of a side reboiler, and an upper heat source of a crude phenol column (CPC) and a phenol finishing column (PFC) is used.

On the contrary, the hydrocarbon removal column (HRC) consuming such a large amount of energy supplies energy (heat source) to reaction parts (1, 2) and a separation part (3) in a phenol preparation process, but has a main downside of losing a heat source due to the presence of uncondensed vapor (6). Accordingly, energy saving consumed in a whole process including minimizing the loss of a heat source by changing operation conditions of various columns such as a hydrocarbon removal column (HRC) is required.

Various methods for purifying phenol are disclosed such that Korean Registration Patent No. 10-0377297 relates to a purification method of phenol which is prepared by a cumene method, and discloses features for improving the performance of a catalyst used during separating phenol by controlling the temperature, the composition, or the like during separating phenol and impurities, and Korean Laid-open Publication Patent No. 10-2006-0130073 also relates to a purification method of phenol, and discloses features for producing a purified phenol steam by decreasing the initial concentration of hydroxyacetone and methylbenzofuran in a phenol steam simultaneously, by contacting a phenol steam containing hydroxyacetone and methylbenzofuran with initial concentrations at 50 to 100° C. with an acidic ion exchange resin. Research for further improvement thereof is conducted from various angles.

DISCLOSURE OF THE INVENTION

Technical Problem

An object of the present invention is to provide a method for purifying phenol by which the amount used of steam may be decreased by minimizing the loss of a heat source, and energy efficiency consumed in a process may be maximized.

Technical Solution

In order to accomplish the object, the present invention provides a method for purifying phenol, including a step of passing impurities including phenol, acetone and hydrocarbon, which are prepared using cumene as a raw material, via a plurality of distillation columns one by one and performing azeotropic distillation, wherein a ratio of phenol and water at the uppermost distillation column in which the azeotropic distillation is performed is from 60:40 to 65:35, in order to optimize separation of the hydrocarbon.

Advantageous Effects

By the method for purifying phenol according to the present invention, the loss of a heat source is minimized, the amount used of steam is reduced, and efficiency of energy consumed in a process may be maximized.

BRIEF DESCRIPTION OF THE DRAWINGS

(A) in FIG. 5 is a diagram showing the recovery quantity of heat varying according to the operation pressure change of a crude phenol column, and (B) in FIG. 5 is a diagram showing the recovery quantity of heat varying according to the operation pressure change of a phenol finishing column (B).

BEST MODE FOR CARRYING OUT THE INVENTION

Hereinafter, the present invention will be described in more detail referring to attached drawings.

Figure 1:
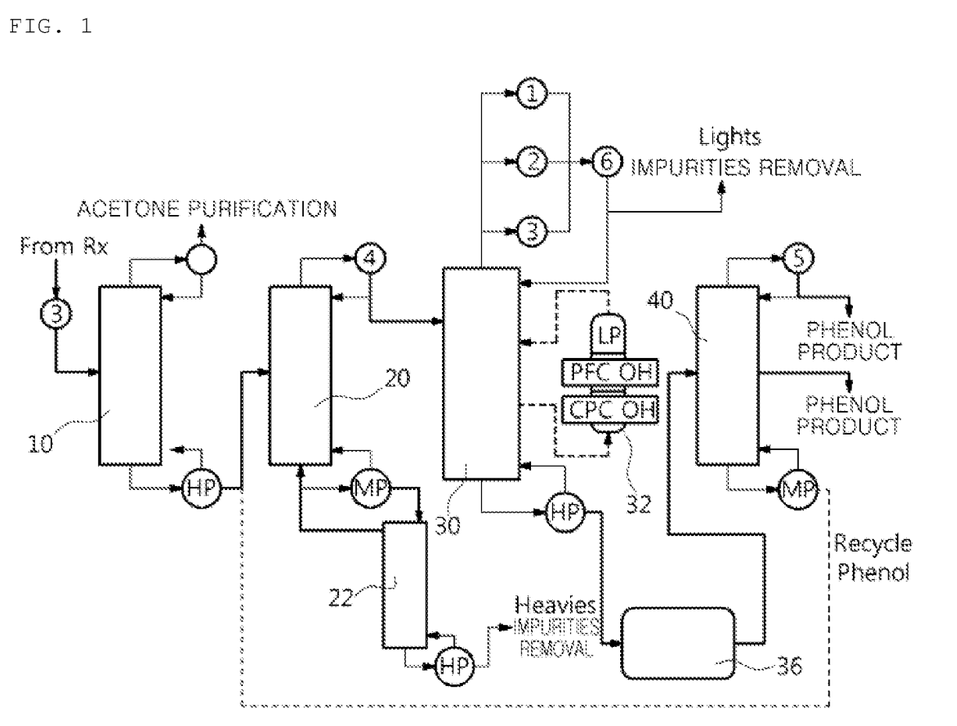
FIG. 1 is a purification process diagram of phenol for explaining a method for purifying phenol according to an embodiment of the present invention.

FIG. 1 is a purification process diagram of phenol for explaining a method for purifying phenol according to an embodiment of the present invention, and referring to FIG. 1, the method for purifying phenol according to the present invention will be explained. The method for purifying phenol according to the present invention includes a step of passing impurities including phenol, acetone and hydrocarbon, which are prepared using cumene as a raw material, via a plurality of distillation columns (10, 20, 22, 30, 40) one by one and performing azeotropic distillation, wherein a ratio of phenol and water at the uppermost distillation column in which the azeotropic distillation is performed is from 60:40 to 65:35, in order to optimize separation of the hydrocarbon.

That is, the present invention relates to a common method for purifying phenol via a plurality of distillation columns, and more particularly, the method includes a step of feeding impurities including phenol, acetone and hydrocarbon, which are prepared using cumene as a raw material into a crude acetone column (CAC, 10) and separating and purifying acetone, a step of feeding impurities including phenol and hydrocarbon, which are discharged via the bottom part of the crude acetone column (10), into a crude phenol column (CPC, 20), discharging and moving phenol and light hydrocarbon to a top part, and discharging heavy impurities including heavy hydrocarbon and a small amount of phenol via a bottom part, a step of feeding the impurities including the phenol and light hydrocarbon into a hydrocarbon removal column (HRC, or a phenol and hydrocarbon separation column, 30) and performing azeotropic distillation to discharge impurities including phenol and a small amount of light hydrocarbon via a bottom part, and discharge impurities including light hydrocarbon and a small amount of phenol via a top part, and a step of feeding the phenol into a phenol finishing column (PFC, 40) and productizing. The present invention is such a common method for purifying phenol in addition to the characteristics of the present invention.

In other words, the plurality of distillation columns include a crude acetone column (CAC, 10) for receiving impurities including phenol, acetone and hydrocarbon, and separating and purifying acetone, a crude phenol column (CPC, 20) for receiving impurities including phenol and hydrocarbon, which are discharged via the bottom part of the crude acetone column, discharging and moving phenol and light hydrocarbon via a top part, and discharging heavy impurities including heavy hydrocarbon and a small amount of phenol via a bottom part, a hydrocarbon removal column (HRC, 30) for receiving the impurities including phenol and light hydrocarbon and performing azeotropic distillation to discharge impurities including phenol and a small amount of light hydrocarbon via a bottom part, and discharge impurities including light hydrocarbon and a small amount of phenol via a top part, and a phenol finishing column (PFC, 40) for receiving the phenol and productizing.

Figure 2:
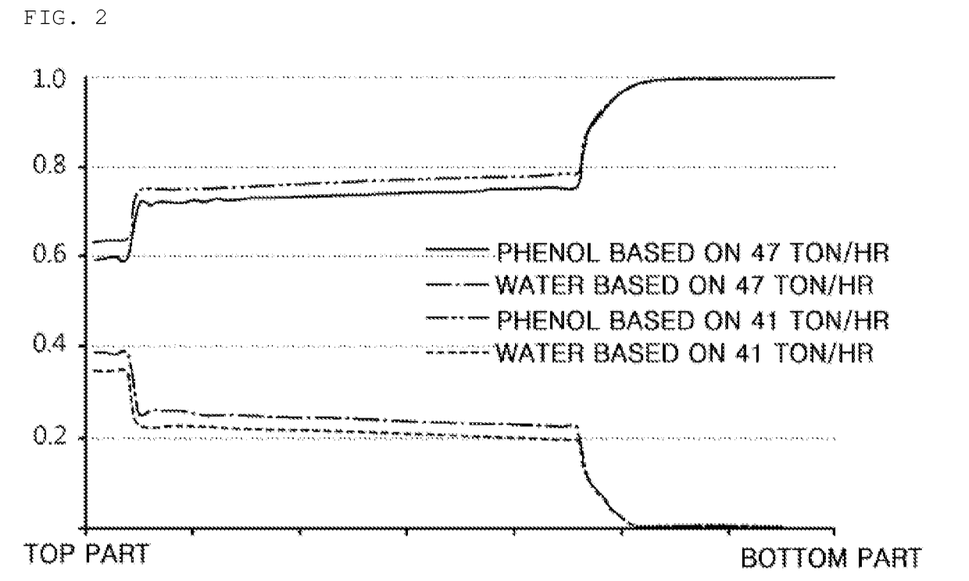
FIG. 2 is a graph showing the composition ratio of phenol and water in a hydrocarbon removal column which is used for a method for purifying phenol according to an embodiment of the present invention.

First, one of the characteristics of the present invention is optimizing the ratio of phenol and water in a distillation column in which the azeotropic distillation is performed, that is, the hydrocarbon removal column (HRC, 30) to optimize the separation of hydrocarbon. FIG. 2 is a graph showing the composition ratio of phenol and water in a hydrocarbon removal column which is used for a method for purifying phenol according to an embodiment of the present invention. As shown in FIG. 2, it can be found that the ratio of phenol and water at the uppermost top (upper when approaches to 0) of the hydrocarbon removal column (HRC, 30) is from 60:40 to 65:35 based on 41 tons of reflux amount per hour, and the ratio of phenol increases when compared to a case based on 47 tons of refluxing amount per hour (a case of conventional phenol purification). That is, in other words, the refluxing amount when the composition of phenol and water is optimized, is decreased when compared to the refluxing amount without optimization, and thus, energy supplied to a column is also decreased.

Meanwhile, it can be found that since the ratio of phenol and water at the top of a side reboiler (32) is optimized when compared to the conventional ratio (that is, since the ratio of phenol increases), energy supplied to a column is decreased, and it can be verified that the composition ratio of phenol and water at the bottom of the side reboiler (32) is similar to the conventional ratio, and no specific advantages are present.

In this way, the optimization of the composition ratio of phenol and water to decrease the refluxing amount per hour means the decrease of energy supplied to a column, and this also means that the separation of hydrocarbon in the hydrocarbon removal column (HRC, 30) is optimized.

Figure 3:
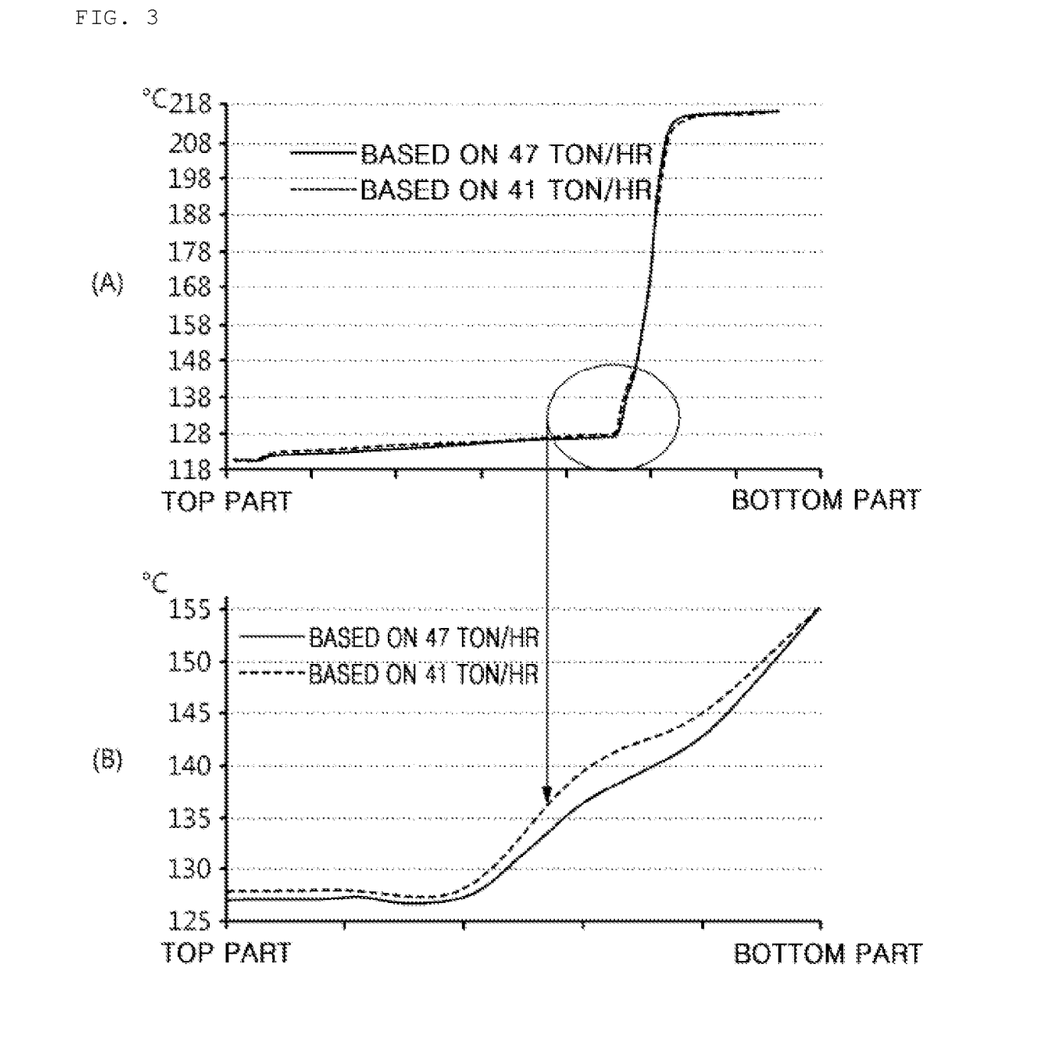
FIG. 3 illustrates graphs showing the temperature change according to the composition change in a hydrocarbon removal column which is used for a method for purifying phenol according to an embodiment of the present invention.

FIG. 3 illustrates graphs showing the temperature change according to the composition change in a hydrocarbon removal column which is used for a method for purifying phenol according to an embodiment of the present invention. (B) in FIG. 3 is an enlarged graph of a blue circle part in (A) in FIG. 3. Meanwhile, if the refluxing amount per hour decreases according to the composition change of phenol and water in the hydrocarbon removal column (HRC, 30), as shown in (B) in FIG. 3, slight increase of the temperature in a partial section of the column is verified, which is due to the increase of the ratio of phenol according to the change of internal composition. Effects of decreasing energy supplied to the hydrocarbon removal column (HRC, 30) by the increased temperature may be attained. That is, in other words, if the ratio of phenol and water is optimized to optimize the separation of the hydrocarbon, temperature is increased, and supplying energy is decreased by the increment of the temperature.

Continuously, according to another characteristic of the present invention, a heat source is supplied to a phenol purification process (CAC feed preheating (3)) and cumene reaction process for producing phenol and acetone (cumene stripper reboiling (1), cumene stripper feed preheating (2)), by using phenolic steam generated during azeotropic distillation in the hydrocarbon removal column (HRC, 30), and remaining phenolic steam after supplied as the heat source is condensed in a condenser (or a heat exchanger, 6), fed to the hydrocarbon removal column (HRC, 30) and reused.

As described above, by using the conventionally discarded phenolic steam as a heat source or reusing thereof after condensing and recovering, the crude acetone column (CAC, 10) may be additionally preheated (that is, additional CAC feed preheating by the phenolic steam), thereby attaining advantages of minimizing unrecovered heat source. In addition, since the crude acetone column (CAC, 10) is already preheated, the quantity of a heat source, for example, a heat source such as steam used in the crude acetone column (CAC, 10) may be decreased.

Figure 4:
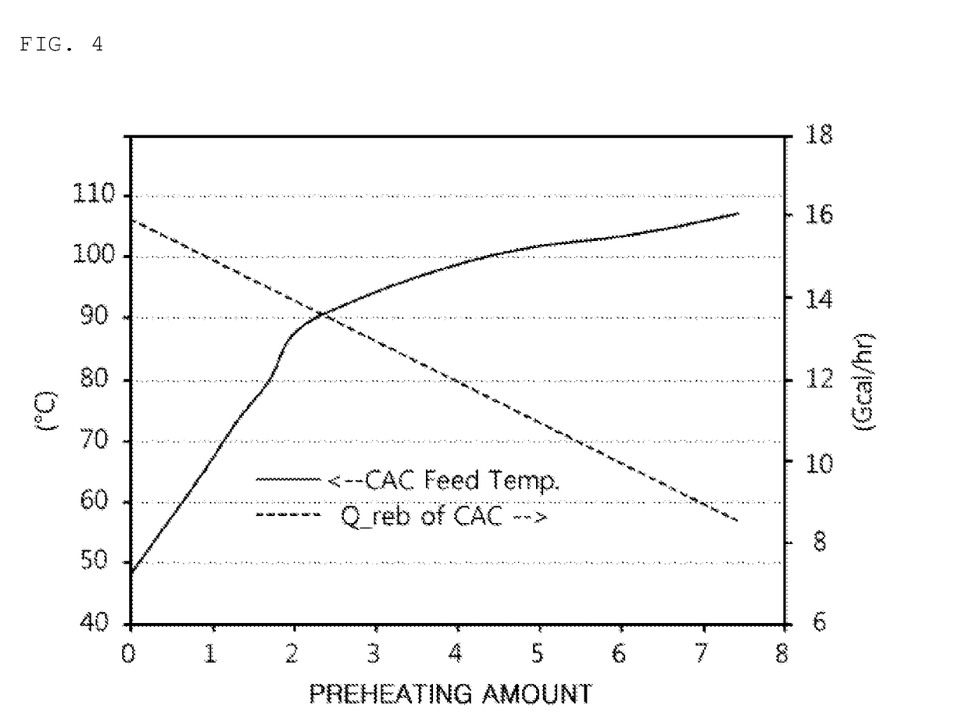
FIG. 4 is a graph showing a Q_reb value when a crude acetone column is preheated by phenolic steam.

FIG. 4 is a graph showing a Q_reb value when a crude acetone column is preheated by phenolic steam. As shown in FIG. 4, if the feed temperature of a column is increased by the phenolic steam, the Q_reb value is decreased. That is, if preheating amount is increased, the feed temperature is also increased, and thus, the quantity of heat used in the crude acetone column (CAC, 10) is decreased. Accordingly, from the results, it can be found that by reusing the recovered phenolic steam in the crude acetone column (CAC, 10) (to be exact, by preheating the feed of the crude acetone column (CAC, 10)), the amount used of the heat source such as steam is decreased.

The last characteristic of the present invention is as follows. If the operation pressure of at least one distillation column selected from the distillation columns, that is, the crude phenol column (CPC, 20) and the phenol finishing column (PFC, 40), is increased, the logarithmic mean temperature difference (LMTD) of a side reboiler (32) is increased, and the quantity of heat recovered is increased. Here, the quantity of heat recovered may be recovered using a condenser (or a heat exchanger) as the phenolic steam produced in the crude phenol column (CPC, 20) and the phenolic steam produced in the phenol finishing column (PFC, 40) in the same manner for recovering phenolic steam produced in the hydrocarbon removal column (HRC, 30). Meanwhile, if the amount recovered of the phenolic steam produced in the crude phenol column (CPC, 20) and the phenol finishing column (PFC, 40) increases, the amount used of energy in the hydrocarbon removal column (HRC, 30) may be also decreased.

Figure 5:
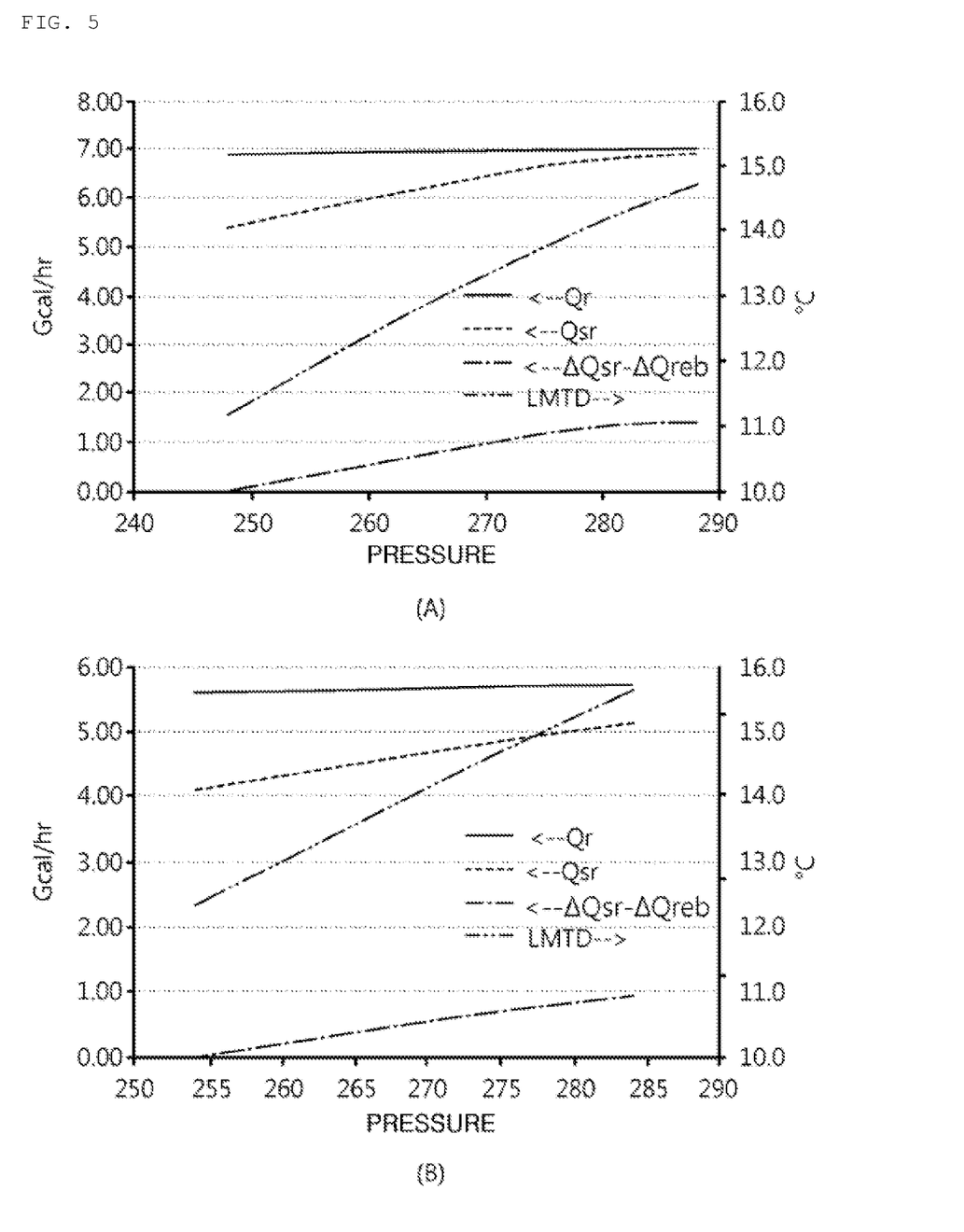

(A) in FIG. 5 is a diagram showing the recovery quantity of heat varying according to the operation pressure change of a crude phenol column, and (B) in FIG. 5 is a diagram showing the recovery quantity of heat varying according to the operation pressure change of a phenol finishing column. As shown in FIG. 5, if the operation pressure of each column is increased, the temperature which is proportional to the increase and decrease of pressure is also increased, and this elevates the logarithmic mean temperature difference (LMTD) of the side reboiler (32), thereby increasing the quantity of heat recovered. In this case, since the quantity of heat is used for the increase of the operation pressure of a column, energy obtained by deducting the increment of the quantity of heat used from the increment of the quantity of heat recovered ($\Delta Qsr-\Delta Qreb$) can be increased or decreased in a whole phenol purification process. Accordingly, by changing the operation conditions of the crude phenol column (CPC, 20) and/or the phenol finishing column (PFC, 40) as described above, the performance efficiency of the side reboiler (32) may be maximized, and in this way, the amount used of a heat source (steam, etc.) of each column is decreased.

Meanwhile, the side reboiler (32) is installed according to the installation position of a common distillation column reboiler including installation corresponding to the side of the hydrocarbon removal column (HRC, 30) or installation at a bottom part, and is a kind of a heat exchanger for reboiling and evaporating liquid come down to the bottom part of the distillation column (hydrocarbon removal column (HRC, 30)).

In FIG. 1, "CPC OH" and "PFC OH" of the side reboiler (32) mean a heat source obtained from the crude phenol column (CPC, 20) and a heat source obtained from the phenol finishing column (PFC, 40), respectively. Since the quantity of heat required for the side reboiling of the hydrocarbon removal column (HRC, 30) is constant, with the increase of the recovering amount of the heat source of the crude phenol column (CPC, 20) and the phenol finishing column (PFC, 40), effects of decreasing the amount used of low pressure (LP) steam is attained.

Meanwhile, the method for purifying phenol according to the present invention may further include a step of transporting heavy impurities including heavy hydrocarbon and a small amount of phenol, which are discharged from the bottom part of the crude phenol column (CPC, 20) to the heavies removal column (RC, 22), recycling the small amount of phenol to the crude phenol column (CPC, 20) via high pressure distillation, and discharging and discarding remaining heavy impurities, as needed. With the additional performance of such processes, even though a small amount, productization or recovering without discarding of phenol which can be used as a heat source is possible. Accordingly, costs consumed during the purification process of phenol may be saved, including reduction of consumption of a heat source.

In addition, the method for purifying phenol according to the present invention may further include a step of passing a small amount of light hydrocarbon which are discharged via the bottom part of the hydrocarbon removal column (HRC, 30) via a resin bed (36) and converting into heavy hydrocarbon and adhering. With the additional performance of such processes, advantages of even easier separation of hydrocarbon may be attained.

Besides, the phenol finishing column (PFC, 40) may recycle a portion of the phenol to the crude phenol column (CPC, 20). This process is for recovering unpurified phenol, and with the performance of such process, the phenol loss of a process may be decreased.

Meanwhile, in the present invention, at the bottom part of each column, as shown in FIG. 1, a heat source generally used in a common column (HP: high pressure steam, MP: middle pressure steam, LP: low pressure steam) is provided. According to the use of the method for purifying phenol according to the present invention, the amount used of HP, MP and LP heat sources which are consumed in a common phenol purification may be decreased.

MODE FOR CARRYING OUT THE INVENTION

Hereinafter, preferred embodiments will be suggested to assist the understanding of the present invention, but the following embodiments are only for illustration of the inventive concept, and various changes and modifications can be made by one ordinary skilled in the art within the technical spirit and scope of the present invention, and such changes and modifications are absolutely included in the claims attached herein.

[Example 1] Purification of Phenol

A purification process included a crude acetone column (CAC), a crude phenol column (CPC), a hydrocarbon removal column (HRC), a phenol finishing column (PFC), a side reboiler, a heavies removal column (RC), and a resin bed. For the optimized separation of hydrocarbon, the composition ratio of phenol and water in the hydrocarbon removal column (HRC) was set to the composition ratio in FIG. 2 (at the uppermost end of the hydrocarbon removal column, from 60:40 to 65:35 based on the refluxing amount of 41 tons per hour), and phenol was purified one by one. Then, the recovery quantity of heat in the hydrocarbon removal column (HRC) O/H and energy amount used in a whole phenol purification process were calculated, losses and energy saving amount were derived, and the results are shown in Table 1 below. Here, the numerical units of the items of HRC O/H recovery quantity of heat analysis and phenol process energy amount used were both Gcal/hr, and the numerical unit of the item of remaining process condition change is torr. In addition, in Table 1 below, the total value of the phenol process energy amount used is obtained by adding up CAC, CPC & RC, HRC SR from LP, HRC reb from HP, and PFC values.

TABLE 1

| | | Example 1 | Example 2 | Example 3 | Comparative Example 1 |
|---|---|---|---|---|---|
| HRC O/H recovery quantity of heat analysis | HRC O/H feed quantity of heat | 22.30 | 22.30 | 22.30 | 25.37 |
| | CAC feed preheating | 6.39 | 7.41 | 7.41 | 6.39 |
| | Cumene stripping | 14.78 | 14.78 | 14.78 | 14.78 |
| | Loss | 1.13 | 0.11 | 0.11 | 4.20 |
| Phenol process energy amount used | CAC | 9.58 | 8.56 | 8.56 | 9.58 |
| | CPC & RC | 6.92 | 6.92 | 6.99 | 6.92 |
| | HRC total SR | 17.80 | 17.80 | 17.80 | 20.20 |
| | HRC SR from CPC O/H & PFC O/H | 8.00 | 8.00 | 10.40 | 9.50 |
| | HRC SR from LP | 9.80 | 9.80 | 7.40 | 10.70 |
| | HRC reb from HP | 6.47 | 6.47 | 6.47 | 7.15 |
| | PFC | 5.59 | 5.59 | 5.70 | 5.59 |
| | Total | 38.36 | 37.34 | 35.12 | 39.94 |
| | Reduction amount | 1.58 | 2.60 | 4.82 | — |
| Process condition change | ΔP of CPC | — | — | 30 | — |
| | ΔP of PFC | — | — | 30 | — |

[Example 2] Purification of Phenol

The same procedure in Example 1 was conducted except for recovering phenolic steam produced during azeotropic distillation in the hydrocarbon removal column (HRC), and feeding thereof to one end of a feed line of impurities including the phenol, acetone and hydrocarbon of the crude acetone column (CAC) for reuse. Then, recovery quantity of heat of the hydrocarbon removal column (HRC) O/H and energy amount used in a whole phenol purification process were calculated, losses and energy saving amount were derived, and the results are shown in the above Table 1.

[Example 3] Purification of Phenol

The same procedure described in Example 2 was conducted except for increasing the operation pressures of the crude phenol column (CPC) and the phenol finishing column (PFC) by 30 torr, respectively, so as to increase the logarithmic mean temperature difference (LMTD) of the side reboiler to increase the quantity of heat recovered. Then, recovery quantity of heat in the hydrocarbon removal column (HRC) O/H and energy amount used in a whole phenol purification process were calculated, losses and energy saving amount were derived, and the results are shown in Table 1 below.

[Comparative Example 1] Purification of Phenol

A purification process was conducted by common operation conditions excluding the conditions of Examples 1 to 3. Then, recovery quantity of heat in the hydrocarbon removal column (HRC) O/H and energy amount used in a whole phenol purification process were calculated, losses was derived, and the results are shown in the above Table 1.

[Examples 1-3 and Comparative Example 1] Evaluation of Efficiency of Energy Used for Phenol Purification As shown in the above Table 1, the loss of the quantity of heat was found to decrease when compared to Comparative Example 1, for Example 1 in which the composition ratio of phenol and water in the hydrocarbon removal column (HRC) was changed (in other words, the optimum composition profile was applied) for the optimized separation of hydrocarbon, Example 2 in which phenolic steam produced during azeotropic distillation was recovered and fed to one end of the feed line of the crude acetone column (CAC) for reuse, and Example 3 in which the operation pressures of the crude phenol column (CPC) and the phenol finishing column (PFC) were increased to increase the logarithm mean temperature difference (LMPT) of the side reboiler to increase the quantity of heat recovered. That is, the loss may be figured out by deducting practically used CAC feed preheating and cumene stripping value from the hydrocarbon removal column (HRC) O/H feed quantity of heat. When compared to the loss of 4.20 of Comparative Example 1, the losses of Examples 1 to 3 were 1.13 to 0.11, and the optimum effects of composition profile may be found. Also, it was secured that the losses of Examples 2 and 3 were smaller than the loss of Example 1, and from the results, the effects obtained by the recovery and reuse of the phenol steam may be found.

In addition, all Examples 1 to 3 were found to have decreased energy amount consumed in a whole process when compared to that of Comparative Example 1 (decreased by 1.58, 2.60 and 4.82 for Examples 1 to 3, respectively). Particularly, it was secured that Example 3 in which the operation pressured of the crude phenol column CPC and the phenol finishing column PFC was increased, showed definitely increased saving amount than Examples 1 and 2. From the results, effects obtained by increasing the operation pressures of the crude phenol column CPC and the phenol finishing column PFC may be found. Meanwhile, among the items in the above Table 1, the CPC and PFC values of Example 3 are somewhat higher than those of Examples 1 and 2, because energy is consumed for the increase of the pressure of each column.

Overall, from the above Example 1, it may be secured that the operation energy of the hydrocarbon removal column HRC and the amount of the phenol steam which was conventionally discarded, may be decreased by optimizing the ratio of phenol and water in the hydrocarbon removal column (HRC). From the above Example 2, it may be secured that the recovering ratio of phenol steam which was conventionally discarded may be increased and at the same time, the operation energy amount of the crude acetone column CAC may be decreased, by condensing residual phenol steam and using thereof for the feed preheating of the crude acetone column CAC. In addition, from the above Example 3, it may be secured that energy amount consumed in a whole process may be saved by the best way by increasing the operation pressures of the crude phenol column CPC and the phenol finishing column PFC.

The invention claimed is:

1. A method for purifying phenol, comprising a step of passing first impurities comprising phenol, acetone and hydrocarbon, which are prepared using cumene as a raw material, through a plurality of distillation columns sequentially and performing azeotropic distillation,
   wherein the plurality of distillation columns comprise:
   a crude acetone column (CAC) for receiving the first impurities comprising phenol, acetone and hydrocarbon and for separating and purifying acetone;
   a crude phenol column (CPC) for receiving second impurities comprising phenol and hydrocarbon discharged from a bottom part of the crude acetone column, for discharging light impurities comprising phenol and light hydrocarbon from a top part, and for discharging heavy impurities including heavy hydrocarbon and phenol from a bottom part;

a hydrocarbon removal column (HRC) for receiving the light impurities comprising phenol and light hydrocarbon and performing azeotropic distillation, for discharging third impurities comprising phenol from a bottom part, and for discharging fourth impurities comprising light hydrocarbon from a top part; and a phenol finishing column (PFC) for receiving the third impurities comprising phenol from the HRC and for productization, and wherein a weight ratio of phenol and water at an uppermost part of the top part of the HRC in which the azeotropic distillation is performed is from 60:40 to 65:35, so that separation of the hydrocarbon can be optimized.

2. The method for purifying phenol of claim 1, wherein a phenolic steam generated during the azeotropic distillation is recovered and reused in a purification process.

3. The method for purifying phenol of claim 2, wherein the recovered phenolic steam preheats a feed of the crude acetone column (CPC).

4. The method for purifying phenol of claim 2, wherein the phenolic steam is recovered in the hydrocarbon removal column (HRC) after being condensed in a condenser.

5. The method for purifying phenol of claim 1, wherein if an operation pressure of the distillation column is increased, a logarithmic mean temperature difference of a side reboiler is increased, and a quantity of heat recovered is increased.

6. The method for purifying phenol of claim 5, wherein the distillation column of which operation pressure is increased, is at least one distillation column selected from the group consisting of the crude phenol column (CPC) and the phenol finishing column (PFC).

7. The method for purifying phenol of claim 1, further comprising a step of transporting the heavy impurities comprising heavy hydrocarbon and phenol discharged from the bottom part of the crude phenol column (CPC) to a heavies removal column (RC), refluxing the phenol to the crude phenol column (CPC) by high pressure distillation in the RC, and discharging and discarding remaining heavy impurities.

8. The method for purifying phenol of claim 1, further comprising a step of passing the light hydrocarbon discharged from the bottom part of the hydrocarbon removal column (HRC) through a resin bed for converting into heavy hydrocarbon and being adsorbed on the resin bed.

9. The method for purifying phenol of claim 1, wherein the phenol finishing column (PFC) refluxes a portion of a phenolic stream to the crude phenol column (CPC) for recovering unpurified phenol.

* * * * *